United States Patent [19]

Bruns et al.

[11] 4,268,443
[45] May 19, 1981

[54] 13,15-DIOXABICYCLO[10.5.0]HEPTADEC-ANES, THEIR PREPARATION, AND THEIR USE IN PERFUME COMPOSITIONS AND AS AN ODORANT

[75] Inventors: Klaus Bruns, Krefeld-Traar; Peter Meins, Mettmann, both of Fed. Rep. of Germany

[73] Assignee: Henkel Kommanditgesellschaft auf Aktien (Henkel KGaA), Düsseldorf-Holthausen, Fed. Rep. of Germany

[21] Appl. No.: 48,504

[22] Filed: Jun. 14, 1979

[30] Foreign Application Priority Data

Jun. 26, 1978 [DE] Fed. Rep. of Germany ....... 2827979

[51] Int. Cl.³ .......................................... C07D 319/08
[52] U.S. Cl. ........................... 260/340.3; 260/343.3 R; 560/126; 568/821; 252/522 R
[58] Field of Search ...................................... 260/340.3

[56] References Cited

U.S. PATENT DOCUMENTS 3,373,136  3/1968  Wicker .......................... 260/340.3
3,686,225  8/1972  Pedersen ....................... 260/340.3
4,124,541  11/1978  Conrad et al. ............... 260/340.3 X Primary Examiner—Ethel G. Love
Attorney, Agent, or Firm—Hammond & Littell, Weissenberger and Muserlian

[57] ABSTRACT

This invention is directed to 13,15-dioxabicyclo[10.5.0-]heptadecanes having the structural formula

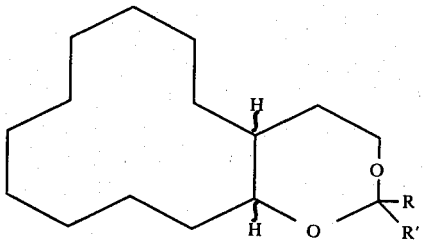

wherein R and $R^1$ are independently hydrogen or a methyl radical. The invention is also directed to their preparation, their use as perfuming agents and as olefactant components in perfume compositions and as an odorant agent for technical products.

2 Claims, No Drawings

13,15-DIOXABICYCLO[10.5.0]HEPTADECANES, THEIR PREPARATION, AND THEIR USE IN PERFUME COMPOSITIONS AND AS AN ODORANT

FIELD OF THE INVENTION

This invention relates to polycyclic dioxaheptadecanes and, more particularly, to 13,15-dioxabicyclo[10.5.0]heptadecanes, and their preparation; perfume compositions containing the same; and a method of imparting pleasant odors to objects with such compositions.

BACKGROUND OF THE INVENTION

Various bicyclo compounds are known. For example, copending U.S. patent application Ser. No. 16,548 filed Mar. 1, 1979, is directed to 13-oxabicyclo[10.3.0]-pentadecane. Applicants have surprisingly prepared 13,15-dioxabicyclo[10.5.0]heptadecanes and have found them to be useful as perfumery agents.

OBJECTS OF THE INVENTION

It is an object of the present invention to provide novel compounds known as 13,15-dioxabicyclo[10.5.0]-heptadecanes. It is also an object of this invention to provide for the preparation of these novel compounds and their use of same as perfumery agents.

These and other objects of the invention will become more apparent as the description thereof proceeds.

DESCRIPTION OF THE INVENTION

It has been found that novel 13,15-dioxabicyclo[10.5.0]heptadecanes of the formula

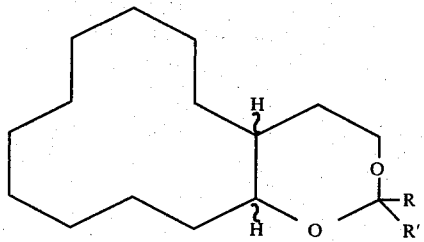

wherein R and $R^1$ are independently hydrogen or a methyl radical, represent valuable new perfumery agents having a warm amber nuance and good odor persistency.

The new compounds according to this invention are synthesized by the following procedure:

Cyclododecanone (I) is condensed with a bromoacetic ester to form the corresponding hydroxyester (II). The hydroxyester is rearranged to the oxabicyclo pentadecane lactone (III) by heating in a strongly acid medium. This lactone is converted with an alkali metal borohydride, such as potassium, sodium or lithium borohydride, in isopropanol to the diol (IV), from which 13,15-dioxabicyclo[10.5.0]heptadecane (V) is obtained by acetalization with paraformaldehyde in ethylene chloride. The 13,15-dioxabicyclo[10.5.0]heptadecane is formed as a mixture of two stereo isomers in a ratio of about 1:25. The synthesis takes place according to the following reaction scheme:

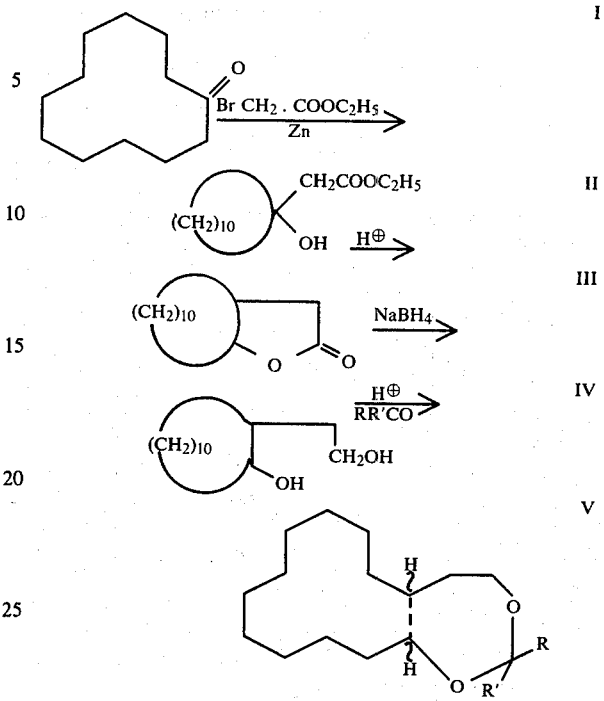

The methyl-substituted 13,15-dioxabicyclo[10.5.0]-heptadecanes are obtained from the diol (IV) by acetalization or ketalization.

More particularly, the invention involves the process for the preparation of 13,15-dioxabicyclo[10.5.0]-heptadecanes which comprises the steps of:

(a) condensing cyclododecanone with an ester of bromoacetic acid to form a cyclododecane-hydroxymethylcarboxylic acid ester;

(b) rearranging said hydroxy-methylcarboxylic acid ester to the cyclododecane-hydroxy-methylcarboxylic acid lactone in the presence of a strong acid;

(c) reducing the resulting lactone by reaction with an alkali metal borohydride to form the corresponding cyclododecane-hydroxy-ethylol;

(d) acetalizing or ketalizing said hydroxy-ethylol to form 13,15-dioxabicyclo[10.5.0]heptadecanes; and (e) recovering said 13,15-dioxabicyclo[10.5.0]heptadecanes.

The useful compounds prepared according to this invention include 13,15-dioxabicyclo[10.5.0]heptadecane, 13,15-dioxa-14-methylbicyclo[10.5.0]heptadecane, and 13,15-dioxa-14,14-dimethylbicyclo[10.5.0]heptadecane. The unsubstituted 13,15-dioxabicyclo-[10.5.0]heptadecane is of particular importance since it is characterized by a warm amber note and has excellent odor persistency. Another advantage of the 13,15-dioxabiocyclo[10.5.0]heptadecanes is that they are readily combinable with new compositions to which they impart a good background and good persistence.

The 13,15-dioxabicyclo[10.5.0]heptadecanes can be mixed with other perfumes in various mixing ratios to form new perfume compositions. In general, they are used in perfume compositions in concentrations of between about 1 and 50% by weight, based on the weight of the entire composition.

Such compositions can be used directly as perfumes or for perfuming cosmetics, such as creams, lotions, toilet water, aerosols, toilet soaps, etc. The compositions can also be used to improve or reodor the odor of technical products, such as washing and cleaning agents, soft rinses, and textile reagents. For perfuming the various products, the compositions are generally added in effective amounts in concentrations of from about 0.05 to 5% by weight. From about 0.05 to 2% by weight suffices for most perfumery purposes, but greater amounts may be needed when used as a reodorant.

The following examples will illustrate the subject of the invention, without limiting it, however, to these examples.

EXAMPLES

Preparation of 13,15-dioxabicyclo[10.5.0]heptadecane (a) Preparation of the hydroxy ester:

A solution of 182 gm (1 mol) of cyclododecanone and 167 gm (1 mol) of ethyl bromoacetate in toluene/benzene (140/160 ml) was added dropwise over a period of four hours, under stirring and at reflux, to a suspension of 33 gm of zinc powder in toluene/benzene (140/160 ml), which had been activated with a few iodine crystals. After completion of the addition, the mixture was heated for an additional two hours at reflux. The zinc powder used was pre-treated as follows: the zinc powder was stirred for about 20 minutes in 10% aqueous hydrochloric acid, then drained off, washed neutral with water, and washed dry with acetone. Subsequently, it was dried under vacuum at 50° C.

After the reaction mixture cooled, unreacted zinc powder was dissolved by stirring and cooling with about 300 ml of ice-cold sulfuric acid (10%). The organic phase was separated, washed with 2 N sodium hydroxide solution, then washed with 2 N sulfuric acid, and finally washed until neutral with water. After drying over sodium sulfate, the solvent was distilled at reduced pressure, and the hydroxy ester obtained was freed from unreacted cyclododecanone under high vacuum by an oil pump vacuum.

(b) Preparation of the lactone:

The above-obtained hydroxy ester raw product (270 gm) was mixed under strong stirring at 60° C. with 1080 ml of an 80% aqueous sulfuric acid. The mixture was intensively stirred at 60° C. for one hour and then poured on ice to cool. The solution was subsequently stirred until the ice was completely melted and then extracted with ether. The ethereal phase was washed with 2 N sodium hydroxide solution and then washed until neutral with water. After drying over sodium sulfate and distilling off the solvent, the lactone was recovered as a crystalline mass.

(c) Preparation of the diol

The above-obtained raw lactone (204 gm) was dissolved in 3600 ml of isopropanol. An amount of 45.6 gm (1.2 mol) of sodium borohydride was added thereto under stirring, and the mixture was stirred for three hours while heating to reflux. After the reaction was completed, the mixture was poured into twice its volume of water. The aqueous mixture was extracted several times with ether. The ethereal extracts were combined and dried. The solvent was driven off, and the raw product was distilled in the vacuum of an oil pump.

The diol obtained was a colorless, viscous liquid; B.P. 0.6 mm Hg, 172°–175° C.

(d) Preparation of 13,15-dioxabicyclo[10.5.0]heptadecane:

The diol obtained (208 gm) was dissolved in 60 ml of ethylene chloride. Then 44.0 gm of paraformaldehyde and one drop of conc. sulfuric acid were added, and the mixture was refluxed for three hours with separation of water. After the reaction was completed, 1.5 gm of sodium carbonate were added. Most of the solvent was removed by evaporation at normal pressure, and the residue was distilled under oil-pump vacuum. The 13,15-dioxabicyclo[10.5.0]heptadecane obtained was a colorless liquid with the following characteristics:

B.P. 0.6 mm Hg, 132° C.

IR (film) 1000 to 1700, max. 1060, 1155/cm (CH—O—CH$_2$—O—CH$_2$)

1H-NMR δ 3.68 (m,2H) (O—C$\underline{H}_2$—O) 4.72 (m,3H) (O—C$\underline{H}_2$—CH$_2$, C$\underline{H}$—O—CH$_2$—O)

The odor was characterized as a warm amber nuance.

Preparation of 14-methyl-13,15-dioxabicyclo(10.5.0)-heptadecane

A mixture of 240 gm (1 mol) of the diol prepared according to (c) above, 90 gm (1 mol) of acetaldehyde dimethyl acetal, and 0.2 gm of p-toluene sulfonic acid was refluxed for five hours at 70° C. After the reaction was completed, the reaction mixture was taken up in ether, washed neutral with 2 N sodium hydroxide solution, washed with water, and then dried over anhydrous sodium sulfate. The ether and methanol were distilled off, and then the residue was distilled in the oil-pump vacuum. The 14-methyl-13,15-dioxabicyclo[10.5.0]heptadecane obtained was a colorless liquid with the following characteristics:

B.P. 0.15 mm Hg, 119°–120° C.

IR (film) 1000 to 1170; max. 1097, 1165/cm (CH—OCHCH$_3$—O—CH$_2$)

1H-NMR δ 3.73 (m, 3H) (O—C$\underline{H}_2$—CH$_2$, C$\underline{H}$—O—CHCH$_3$) 4.88 (m, 1H) (O—C$\underline{H}$CH$_3$)

The odor of the product was characterized as a warm amber, wood, fruit-fragrance and was of much lesser intensity than that of the unsubstituted compound.

EXAMPLE 1

| Perfume Composition Virginia-Tobacco base | Parts by weight |
| --- | --- |
| 13,15-dioxabicyclo[10 . 5 . 0]heptadecane | 150 |
| Boisamerene forte (Henkel KGaA) | 250 |
| Isogeranyl nitrile | 200 |
| Methylionone | 100 |
| Vetiveryl acetate | 100 |
| 2-Acetyl-4-isopropyl-5,5-dimethyl-1,3-dioxne | 100 |
| Pentadecanolide 10% in DEP | 50 |
| Cumarin | 25 |
| Galazolide (IFF) | 25 |

Compounds methyl-substituted in 14-position can be used in place of 13,15-dioxabicyclo[10.5.0]heptadecane.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A 13,15-dioxabicyclo[10.5.0]heptadecane of the formula

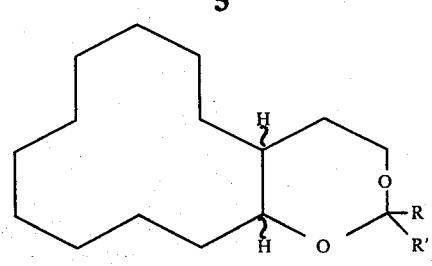
wherein R and R[1] are independently hydrogen or a methyl radical.
2. 13,15-dioxabicyclo[10.5.0]heptadecane.